United States Patent [19]

Correale et al.

[11] Patent Number: 4,933,504
[45] Date of Patent: Jun. 12, 1990

[54] PROCESS FOR THE PREPARATION OF MONO-ETHERS OF HYDROQUINONES

[75] Inventors: Mariano Correale, Bonate Sotto; Pietro Panseri, Bergamo; Ugo Romano, Vimercate; Francesco Minisci, Milan, all of Italy

[73] Assignee: Enichem Synthesis S.p.A., Palermo, Italy

[21] Appl. No.: 275,968

[22] Filed: Nov. 25, 1988

[30] Foreign Application Priority Data

Nov. 27, 1987 [IT] Italy ................... 22787 A/87

[51] Int. Cl.$^5$ .......................................... C07C 41/18
[52] U.S. Cl. ................... 568/650; 568/640; 568/644
[58] Field of Search ............... 568/648, 650, 629, 638, 568/658, 640, 644

[56] References Cited

U.S. PATENT DOCUMENTS 4,568,497 2/1986 Mendoza et al. ............ 568/648

FOREIGN PATENT DOCUMENTS 1557237 12/1979 United Kingdom .

Primary Examiner—Bruce Gray
Attorney, Agent, or Firm—Oblon, Spivak, McClelland, Maier & Neustadt

[57] ABSTRACT

Mono-ethers of hydroquinones of formula (I)

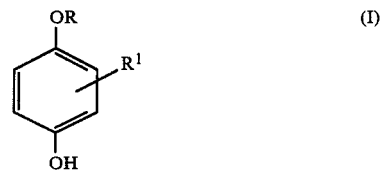

wherein
R represents alkyl, alkoxy-alkyl, cycloalkyl, aryl-alkyl, or cycloalkyl-alkyl, and
R$^1$ is hydrogen or alkyl, cycloalkyl, aryl-alkyl, or cycloalkyl-alkyl, are prepared by contacting the corresponding hydroquinones with the corresponding alcohols ROH, in the presence of a catalytic mixture consisting of
(a) a strong acid
(b) a halogen or a hydrohalic acid selected from HBr, HI, I$_2$, and Br$_2$, and
(c) H$_2$O$_2$ in a molar amount lower than that of the starting hydroquinone.

10 Claims, No Drawings

PROCESS FOR THE PREPARATION OF MONO-ETHERS OF HYDROQUINONES

The present invention refers to a process for the preparation of mono-ethers of hydroquinones, starting from the corresponding hydroquinones and alcohols, by contacting them in the presence of a catalytic mixture comprising
- (a) a strong acid
- (b) a halogen or a hydrohalic acid selected from HBr, HI, $I_2$, and $Br_2$, and
- (c) $H_2O_2$ in a molar ratio to the starting hydroquinone lower than 1.

More particularly, the present invention relates to a process for the preparation of a mono-ether of general formula (I)

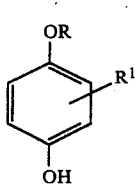

(I)

wherein
R represents alkyl, alkoxy-alkyl, cycloalkyl, aryl-alkyl, or cycloalkyl-alkyl, and
$R^1$ is hydrogen, alkyl, cycloalkyl, aryl-alkyl, or cycloalkyl-alkyl,
which comprises contacting the corresponding hydroquinone of formula (II)

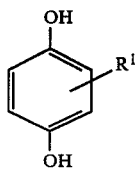

(II)

wherein
$R^1$ is as defined above, with the corresponding alcohol of formula ROH, in the r presence of a catalytic mixture comprising
- (a) a strong acid
- (b) a halogen or a hydrohalic acid selected from HBr, HI, $I_2$, and $Br_2$, and
- (c) $H_2O_2$ in a molar amount lower than that of the starting hydroquinone.

For the purposes of the present invention the term "alkyl" substantially designates a straight or branched ($C_1$–$C_{18}$)alkyl radical, e.g. methyl, ethyl, propyl, iso-propyl, butyl, iso-butyl, iso-pentyl, hexyl, octyl, dodecyl, etc., and, preferably, a straight or branched ($C_1$–$C_{10}$)alkyl radical. The term "alkoxy-alkyl" typically identifies an alkyl radical, as defined above, which bears one or more ($C_1$–$C_8$)alkoxy substituents, e.g. methoxy-ethyl, ethoxy-ethyl, methoxy-butyl, etc..

The term "cycloalkyl" designates a 5-, 6-, 7-, or 8-membered cycloaliphatic radical which may be substituted with one or more ($C_1$–$C_8$)alkyl groups, e.g. cyclopentyl, cyclohexyl, cycloheptyl, 4-methyl-cyclopentyl, etc..

The term "aryl-alkyl" typically identifies a phenyl-alkyl radical wherein the alkyl moiety may be straight or branched and contain from 1 to 8 carbon atoms and the phenyl group may bear one or more substituents, which do not interfere with the reaction, e.g. straight or branched lower alkyl or lower alkoxy groups, e.g. benzyl, 4-methyl-benzyl, 2-methoxy-benzyl, phenyl-ethyl, etc..

Finally, as for the term "cycloalkyl-alkyl", both the alkyl and the cycloalkyl moieties are as defined above. It is known from G.B. Patent No. 1,557,237 that mono-alkyl ethers of hydroquinones can be prepared by reacting an aliphatic alcohol with a mixture of a hydroquinone and the corresponding quinone, in the presence of an acid dehydration catalyst, which is employed with the aim at carrying out the reaction in substantially anhydrous conditions.

According to said British patent, in order to get selectively a mono-alkyl etherification, the weight ratio between the starting hydroquinone and the corresponding quinone (which—by the way—may be generated in situ) must be kept within a fixed range (from 5:1 to 20:1).

It has now been found that it is possible to achieve mono-etherification of hydroquinones, starting from the corresponding hydroquinones and alcohols, with high conversion yields and very high selectivities, with no need to carry out the reaction under anhydrous conditions, and no need also to add the corresponding quinones or check their generation in situ in a strictly fixed ratio within the prescribed range.

As anticipated, therefore, object of the present invention is a process for the preparation of mono-ethers of hydroquinones of formula (I) which comprises reacting a hydroquinone of above formula (II) with an alcohol R-OH, in the presence of a catalytic mixture comprising:
- (a) a strong acid
- (b) a halogen or a hydrohalic acid selected from HBr, HI, $I_2$, and $Br_2$, and
- (c) $H_2O_2$ in a molar ratio with respect to the starting hydroquinone, lower than 1, and, preferably, from 0.05 to 0.5.

As the reaction may occur in anhydrous conditions as well as in the presence of fairly high amounts of water, $H_2O_2$, in the above molar proportion, may be added as an aqueous solution thereof.

As the strong acid (a), any strong acid, either organic or inorganic, which cannot be oxidised by $H_2O_2$, can conveniently be employed.

Suitable acids include, for instance, methanesulphonic acid, p-toluene-sulphonic acid, tri-fluoro-methanesulphonic acid, trifluoroacetic acid, perchloric acid, and, preferably, sulphuric acid. The amount of strong acid which is employed may range from 0.05 to 1 mole per mole of starting hydroquinone.

It is alternatively possible to use as strong acid (a), a sulphonated resin acid, i.e. an inert polymer matrix, e.g. polystyrene, containing sulphonic groups in acidic form. Among these resins, those available under the trade-names Nafion ® or Amberlist ® 15, are preferred.

Finally, as for halogen or hydrohalic acid (b), catalytic amounts, typically from 0.05 to 1%, by mole, with respect to the starting hydroquinone, are sufficient to afford satisfactory results.

While, in line of principle, an equimolar proportion of the alcohol and the hydroquinone is required by the reaction stoichiometry, actually the use of an excess alcohol with respect to the hydroquinone is preferred, and of a strong excess even more preferred.

More particularly, the reaction will be carried out using a molar ratio of alcohol to hydroquinone from 3:1 to 50:1 and, more preferably, from 7:1 to 15:1.

The reaction is preferably carried out without the addition of an organic solvent as the excess alcohol may work as the reaction solvent.

It is possible, however, to perform the reaction in the presence of an additional solvent. In this case, a suitable solvent will be selected from the group consisting of non-polar inert organic solvents (e.g. toluene, benzene, aliphatic hydrocarbons, and the like solvents).

The reaction, which can be carried out at a temperature from 0 to 150° C. and, more conveniently, from 40° to 0° C., is generally complete in a few hours (4–12).

When the reaction is over, the mixture is neutralized by the addition of an alkaline or alkaline-earth metal base, and the acid (a) corresponding salt that precipitates is removed.

When a sulphonic resin is employed instead of the acid, it can be removed by simple filtration.

The desired product is then recovered by fractional distillation or by extraction with a suitably selected extracting solvent. Solvents which may conveniently be employed for separating the obtained mono-ether from the unconverted hydroquinone, include, for instance, optionally halogenated aliphatic or aromatic hydrocarbons, e.g. toluene, chlorobenzene, dichloroethane, etc..

In the actual practice, the reaction may be carried out either adding the hydroquinone of formula (II) to a solution of the catalytic mixture in the alcohol ROH or, vice-versa, adding $H_2O_2$ to a solution of the other components of the catalytic mixture and of the starting hydroquinone in the alcohol ROH, and stirring, preferably at the reflux temperature of the reaction mixture, for a few hours. The reaction mixture is then cooled to room temperature and the desired product is recovered as described above.

The following examples are included to further illustrate the process of the invention in some representative embodiments thereof. They are not intended to be interpreted as a limitation to the scopes of the invention itself.

EXAMPLE 1

The following reactants are charged, at room temperature, into a 1000-ml glass reactor:

hydroquinone (100 g, 0.9082 mol), $CH_3O_3OH$ (500 ml corresponding to 396.4 g, 12.3720 mol), 96% $H_2SO_4$ (20.80 g, 0.2036 mol), and 57% HI (0.208 g, 0.000927 mol).

The obtained solution is heated to 66° C. (temperature of incipient reflux) and kept at this temperature during the addition of 60% $H_2O_2$ (6.82 g, 0.1203 mol) in 4 h and 30′.

When the addition of the $H_2O_2$ solution is over, the reaction mixture is stirred at 66° C. for additional 30 minutes and then cooled to room temperature.

The reaction mixture is then neutralized with sodium bicarbonate, the precipitated sodium salt is removed by filtration and the filtrate is analyzed by gas-liquid chromatography (GLC) to determine the amount of obtained product and that of the unconverted starting hydroquinone. From these data the hydroquinone %conversion and the reaction selectivity (as the % molar ratio between the obtained mono-ether and the converted hydroquinone) can be easily calculated.

72.93 g of the desired hydroquinone mono-methyl ether (HQMME) are obtained.

Hydroquinone conversion : 68.98%.
Selectivity to HQMME : 93.77%.

The mono-methyl ether and the unconverted hydroquinone are then recovered by distilling off methanol, adding toluene and recovering the insoluble hydroquinone from the toluene solution of HQMME, by filtration.

HQMME is then obtained from the toluene solution by simple distillation.

EXAMPLE 2

The reaction is carried out by following exactly the procedure of example 1 but starting from a mixture containing also water (12 g) (actually 61% H (0.2036 mol) instead of 96% $H_2SO_4$ is employed).

As determined by gas-liquid chromatography of the end reaction mixture, 70.1 g of hydroquinone mono-methyl ether (HQMME) are obtained.

Hydroquinone conversion : 67.65%.
Selectivity to HQMME : 92.99%.

The product is recovered by distillation.

EXAMPLE 3

The reaction is carried out by following exactly the procedure of example 1 but starting from a mixture containing also water (20 g) (actually 49% $H_2SO_4$ (0.2036 mol) instead of 96% $H_2SO_4$ is used).

As determined by GLC analysis of the end reaction mixture, 66.28 g of hydroquinone mono-methyl ether (HQMME) are obtained.

Hydroquinone conversion : 62.03%.
Selectivity to HQMME : 94.80%.

EXAMPLE 4

The reaction is carried out by following substantially the same procedure of example 1 but using 60% $HCLO_4$ (68.18 g, 0.4072 mol) instead of 96% $H_2SO_4$. Furthermore, $H_2O_2$ is added in a lump at 66° C., and the reaction mixture is then stirred at 66° C. for 5 h.

As determined by GLC analysis of the end reaction mixture, 92.33 g of hydroquinone mono-methyl ether (HQMME) are obtained.

Hydroquinone conversion : 86.89%.
Selectivity to HQMME : 94.26%.

EXAMPLE 5

The reaction is carried out by following exactly the procedure of example 1 but charging 0.416 g of 57% HI (0.001854) and 13.64 g of 60% $H_2O_2$ (0.2406 mol).

As determined by GLC analysis of the end reaction mixture, 83.96 g of hydroquinone mono-methyl ether (HQMME) are obtained.

Hydroquinone conversion : 92.50%.
Selectivity to HQMME : 80.52%.

EXAMPLE 6

The reaction is carried out by following exactly the procedure of example 5 but charging 0.2036 moles of aqueous 61% $H_2SO_4$.

As determined by GLC analysis of the end reaction mixture, 81.59 g of hydroquinone mono-methyl ether (HQMME) are obtained.

Hydroquinone conversion : 91.06%.
Selectivity to HQMME : 79.48%.

EXAMPLE 7

The reaction is carried out by following exactly the procedure of example 6 but charging 0.235 g of $I_2$ (0.000927) instead of 0.416 g of 57% HI.

As determined by GLC analysis of the end reaction mixture, 82.65 g of hydroquinone mono-methyl ether (HQMME) are obtained.

Hydroquinone conversion : 93.56%.
Selectivity to HQMME : 78.36%.

EXAMPLE 8

The reaction is carried out by following exactly the procedure of example 5 but charging $C_2H_5OH$ (570 g, 12.3720 mol) instead of $CH_3OH$.

$H_2O_2$ is added to the reaction mixture in one lump at 80° C., and the reaction mixture is then stirred at 80° C. for 5 h.

As determined by GLC analysis of the end reaction mixture, 58.00 g of hydroquinone mono-ethyl ether (HQMEE) are obtained.

Hydroquinone conversion : 62.00%.
Selectivity to HQMEE : 74.56%.

EXAMPLE 9

The reaction is carried out by following exactly the procedure of example 8 but charging 917 g of n-butyl alcohol (12.3720 mol) instead of ethyl alcohol.

As determined by GLC analysis of the end reaction mixture, 53.55 g of hydroquinone mono-butyl ether (HQMBE) are obtained.

Hydroquinone conversion : 44.89%.
Selectivity to HQMBE : 79.02%.

EXAMPLE 10

The following reactants are charged, at room temperature, into a 100-ml glass reactor: hydroquinone (15 g, 0.1362 mol), $CH_3OH$ (47.4 g, 1.4794 mol), dry Amberlist ® 15 (3 g, corresponding to 0.0147 H+ eq.), and 57% HI (0.0634 g, 0.000278 mol). The reaction mixture is heated to 66° C. and maintained at this temperature.

60% $H_2O_2$ (2.046 g, 0.03608 mol) is then added in one lump and the reaction mixture is stirred at 66° C. for 5 hours.

As determined by GLC analysis of the end reaction mixture, 10.21 g of HQMME are obtained.

Hydroquinone conversion : 70.26%.
Selectivity to HQMME : 86%.

We claim:

1. A process for the preparation of a mono-ether of formula (I)

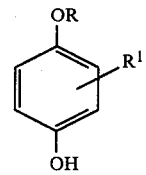

wherein
R represent alkyl, alkoxy-alkyl, cycloalkyl, arylalkyl, or cycloalkyl-alkyl, and
$R^1$ is hydrogen, alkyl, cycloalkyl, aryl-alkyl, or cycloalkyl-alkyl, which consists essentially of reacting the corresponding hydroquinone of formula (II)

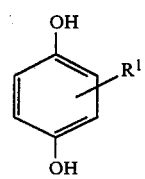

wherein
$R^1$ is as defined above, with the corresponding alcohol of formula ROH, wherein R is as defined above, in the presence of a three component catalytic mixture consisting of
(a) a strong acid selected from the group consisting of sulphuric acid, p-toluenesulphonic acid, perchloric acid, methane-sulphonic acid, trifluoromethane-sulphonic acid, trifluoroacetic acid and a sulphonated resin acid,
(b) a halogen or a hydrohalic acid selected from the group consisting of $Br_2$, $I_2$, HBr and HI, and
(c) $H_2O_2$ in a molar amount lower than the molar amount of the starting hydroquinone.

2. The process of claim 1 wherein the strong acid (a) is a sulphonated resin.

3. The process of claim 1 wherein the molar ratio of strong acid (a) to starting hydroquinone is from 0.05 to 1.

4. The process of claim 1 wherein the amount of halogen or hydrohalic acid (b), by mole, is from 0.05 to 1% of the starting hydroquinone.

5. The process of claim 1 wherein the molar ratio of $H_2O_2$ c) to starting hydroquinone is from 0.05 to 0.5.

6. The process of claim 1 wherein the molar ratio of alcohol ROH to starting hydroquinone is from 3 to 50.

7. The process of claim 6 wherein said molar ratio is from 7 to 15.

8. The process of claim 1 wherein the reaction is carried out at a temperature of from 0° to 150° C.

9. The process of claim 8 wherein said temperature is from 40° to 80° C.

10. The process of claim 1 wherein R is alkyl.

* * * * *